US012616847B2

(12) United States Patent
Kim et al.

(10) Patent No.: US 12,616,847 B2
(45) Date of Patent: May 5, 2026

(54) PHOTODYNAMIC THERAPY AND MICROWAVE THERAPY FUSION SYSTEM

(71) Applicant: KWANGWOON UNIVERSITY INDUSTRY-ACADEMIC COLLABORATION FOUNDATION, Seoul (KR)

(72) Inventors: Nam-Young Kim, Gwangju-si (KR); Eun-Seong Kim, Gwangju-si (KR); Maxim Alexandrovich Pugachevskii, Kursk (RU)

(73) Assignee: KWANGWOON UNIVERSITY INDUSTRY-ACADEMIC COLLABORATION FOUNDATION, Seoul (KR)

( * ) Notice: Subject to any disclaimer, the term of this patent is extended or adjusted under 35 U.S.C. 154(b) by 426 days.

(21) Appl. No.: 18/301,371

(22) Filed: Apr. 17, 2023

(65) Prior Publication Data

US 2024/0001140 A1     Jan. 4, 2024

(30) Foreign Application Priority Data

Jun. 30, 2022     (KR) ........................ 10-2022-0080469

(51) Int. Cl.
    *A61N 5/06*          (2006.01)
    *A61B 18/18*         (2006.01)
(52) U.S. Cl.
    CPC .......... *A61N 5/062* (2013.01); *A61B 18/1815* (2013.01); *A61N 2005/063* (2013.01)
(58) Field of Classification Search
    CPC .......... A61N 5/062; A61N 5/02; A61N 5/022;

A61N 2005/063; A61N 2005/0651; A61N 1/36002; A61B 18/1815; A61B 2018/00994; A61K 41/0023
USPC ........................................................ 607/101
See application file for complete search history.

(56) References Cited

U.S. PATENT DOCUMENTS

| | | | |
|---|---|---|---|
| 8,328,785 B2 * | 12/2012 | Bensaoula | ........... A61N 5/0601 604/500 |
| 2010/0049177 A1 * | 2/2010 | Boone, III | ........... A61H 9/0057 606/9 |
| 2018/0296595 A1 * | 10/2018 | Grimm | ................... A61P 35/02 |

FOREIGN PATENT DOCUMENTS

| | | | |
|---|---|---|---|
| KR | 10-2494745 B1 | 2/2023 | |
| WO | WO-2019147185 A1 * | 8/2019 | .............. H02J 50/20 |

* cited by examiner

*Primary Examiner* — Beverly M Flanagan
(74) *Attorney, Agent, or Firm* — Sughrue Mion, PLLC

(57)          ABSTRACT

A photodynamic therapy and microwave therapy fusion system is provided. The system includes photosensitizers transplanted or attached to the biological tissues of a site in which cancer develops, have specific indirect energy band gaps so as to perform photodynamic therapy for the site in which the cancer develops; and a microwave assisted photodynamic therapy (MWAPDT) controller connected to a personal computer (PC) and adapted to allow a microwave frequency of 5.3 GHz to 10 GHz emitted from a microwave probe or an optic ray emitted from a fiber optic probe to be irradiated onto the biological tissues of the site in which the cancer develops, to which the photosensitizers are attached, so as to perform microwave therapy for the site in which the cancer develops.

4 Claims, 11 Drawing Sheets

Problems of existing cancer treatment

✓ Drug efflux increases
✓ Anti-apoptotic protein revelation increases
✓ Target protein denaturalization
✓ Low effectiveness in cold tumors Occurrence of cancer metastasis and recurrence by anticancer drug resistance ◇ Photonic nanomaterials A method for inducing irreversible cancer cell death through phototherapy using the photosensitizer has been in the limelight.

Photodynamic therapy (PDT)

Photodynamic therapy(PDT) is a treatment in which photosensitizers are applied to a target tumor locally, activated with light absorbed thereto, and generate reactive oxygen species (ROS) to kill the target tumor.

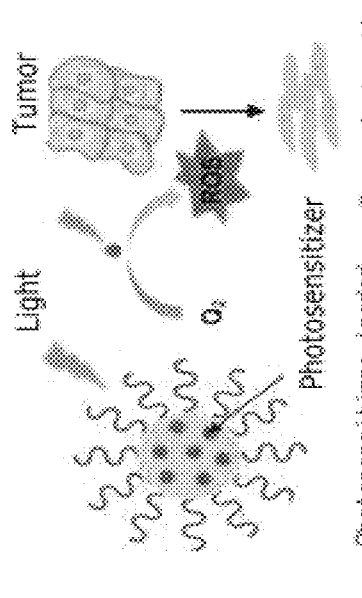

Photothermal therapy (PTT)

Photothermal therapy (PTT) is a treatment in which photosensitizers are applied to a target tumor locally, absorb light applied thereto, and transform the light into heat to kill the target tumor.

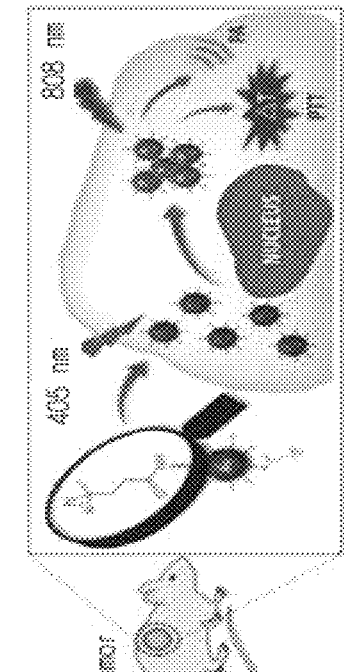

FIG. 2

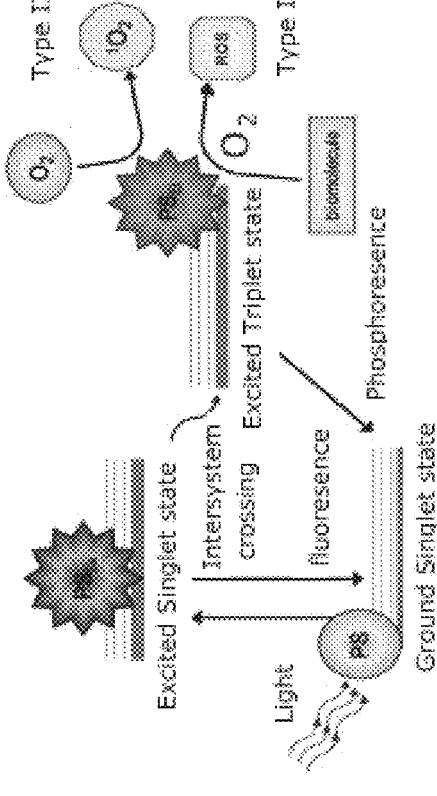

Process of Photodynamic therapy

- Two individually non-toxic components brought together to ca harmful effects on cells and tissues:
  1) Photosensitizing agent 2) Light of specific wavelength

Reaction Mechanisms

- Type 1:
  - Direct reaction with substrate (cell membrane or molecule)
  - Transfer of H atom to form radicals
  - Radicals react with $O_2$ to form oxygenated products

- Type 2:
  - Transfer of energy to to form $^1O_2$

FIG.4

Microwave Therapy
- Electromagnetic field of ultrahigh frequency (up to 3GHz), radiated by a special probe, leads to heating and irradiation of the tumor
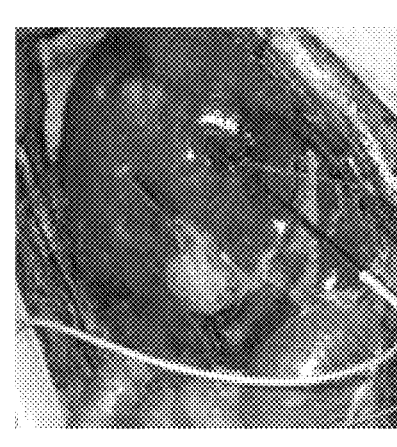
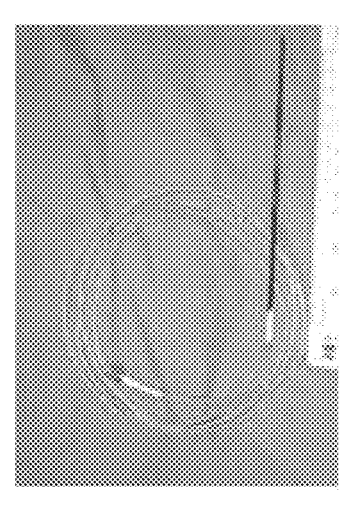
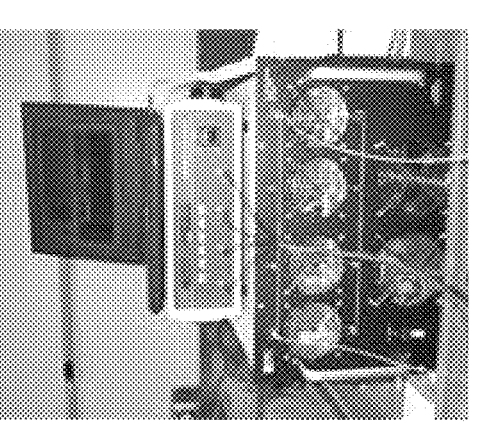
Single Probe
- Vivant Medical
- 13g,15cm dipole antenna
- 915MHz generator
- Fiberoptic temperature monotor
FIG.5

Microwave Therapy
with nano-sized MW absorbers

*FACILITY FEATURES* ⇒ *METHOD ADVANTAGES*

1. Small average power -> safety of living cells in absence of the local MW absorbers 2. Small pulse duration -> local action without significant heat transfer 3. High pulse power -> several possible ways of the wave energy conversion into heating, including breakdown mechanisms 4. Wavelength in cm region -> possibility to increase the MW absorption efficiency using resonance or quasi-resonance conditions Main idea is the selective cancer cell destruction

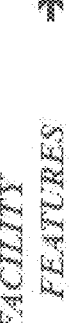
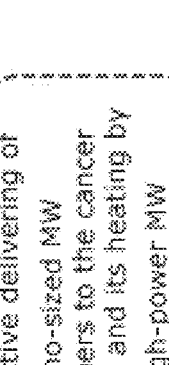
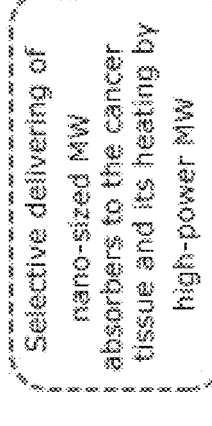

Selective delivering of nano-sized MW absorbers to the cancer tissue and its heating by high-power MW ⇧ ⇧ ⇧
MW radiation

FIG.7

PHOTODYNAMIC THERAPY AND MICROWAVE THERAPY FUSION SYSTEM

CROSS-REFERENCE TO RELATED APPLICATION

This application claims priority to Korean Patent Application No. 10-2022-0080469 filed on Jun. 30, 2022, in the Korean Intellectual Property Office, the entire disclosure of which is incorporated herein by reference.

TECHNICAL FIELD

The present invention relates to a photodynamic therapy and microwave therapy fusion system (hereinafter, referred to as PDTMTFS) capable of allowing photosensitizers having specific indirect energy band gaps to be attached to a target tumor to locally treat solid cancer and, under the control of a microwave assisted photodynamic therapy (hereinafter, referred to as MWAPDT) controller, making use of i) photodynamic therapy (PDT) in which the optic ray emitted from a fiber optic probe is irradiated onto the target tumor so that reactive oxygen species (ROS) or heat is generated primarily by the photosensitizers as photocatalysts to locally remove the target tumor, and ii) microwave therapy in which a microwave is generated from a microwave generator, a microwave transmitter, and an antenna of a microwave probe that irradiate a specific frequency of 5.3 GHz to 10 GHz to vibrate±phonons generated by the indirect energy band gaps from the photosensitizers and generate heat, so that the target tumor is removed and cancer metastasis and recurrence are prevented from occurring. The PDTMTFS is capable of making use of both of ROS and heat capable of inducing irreversible cancer cell death to prevent cancer metastasis and recurrence from occurring by anticancer drug resistance as a problem in a cancer treatment such as existing cancer chemotherapy, thereby providing more effective cancer therapy.

BACKGROUND ART

As the proportion of older people is increasing, the number of patients with cancer, cerebrovascular diseases, heart diseases, and diabetes is increasing. In specific, the high incidence rate of a brain tumor in cranial node appears, i.e., in older patient order of the 50s, 60s, and 70s.

Cancer is a leading cause of death worldwide, and cancer treatments such as surgery, chemotherapy, radiation therapy, immunotherapy, gene therapy, and the like have been developed. Further, the PDT has been introduced to treat all types of cancers.

The PDT is a treatment in which light having a specific wavelength is absorbed to photosensitizers to thus generate ROS or heat in an excited state through an energy transfer mechanism, $E=h\nu$, so that the photosensitizers have chemical reactions with the ROS generated to allow free radicals generated by single oxygen to selectively kill cancer cells, without giving any pain to a patient, or to allow the heat generated from the photosensitizers to kill cancer cells.

Recently, energy-based minimal invasive cancer therapy has been studied to kill a tumor being in a natural state. As the minimal invasive cancer therapy, photodynamic therapy (PDT) using optic ray and sono-dynamic therapy (SDP) using ultrasonic waves are used. The PDT is a treatment in which photosensitizers are injected into a body and laser light (optic ray) of a specific wavelength is irradiated onto an area to be treated, thereby treating a tumor. In this case, the PDT is selectively applied only to the area to be treated, has rare side effects, and is repeatedly performed, thereby improving surgical effectiveness. Further, the PDT can be performed, together with other therapies such as surgical therapy, radiation therapy, chemotherapy, and the like.

One of conventional technologies relating thereto is disclosed in Korean Patent Publication Application No. 10-2021-0043472 entitled "Photosensitization transition materials for brain cancer treatment or brain cancer removal surgery, microwave microchip for inducing movement of brain cancer cell, and use thereof". Another conventional technology relating thereto provides a transplantation composition in a tumor for cancer therapy, a transplantation kit having the same, and cancer therapy having the same, and in this case, the transplantation composition includes photosensitizers selected from the group consisting of $TiO_2$, $ZrO_2$, $HfO_2$, and combinations thereof.

The term "photosensitizers" used in the specification are substances that are excited when the optic ray having a specific wavelength is irradiated thereonto to generate a fluorescence signal or react with surrounding substrates or oxygen to produce the ROS. The produced ROS kill or necrotize surrounding cancer cells to provide local cancer therapy effectiveness. However, the existing photosensitizers may generate photosensitive reactions such as burn, edema, red spots, DNA mutation, and the like, and have difficulties in clinical application because of non-selective transfer to the tissues of a tumor. To solve these problems, the photosensitizers may be selected from the group consisting of $CeO_2$, $TiO_2$, $ZrO_2$, $HfO_2$, and combinations thereof.

The conventional transplantation composition in a tumor is injected directly into a cancer tissue area or intravenously injected into a body in a parenteral administration method through an intravenous infusion. The composition for the parenteral administration can be made in the form of particles or powder, dispersed and/or dissolved in a pharmaceutically allowable carrier, for example, sterile purified water, a buffer solution of approximately pH 7, or a saline solution, and injected into the body. If necessary, the composition may include common additives such as a preservative agent, a stabilizing agent, and the like.

Further, the conventional transplantation kit in a tumor for cancer therapy is provided to have the photosensitizers selected from the group consisting of $CeO_2$, $TiO_2$, $ZrO_2$, $HfO_2$, and combinations thereof.

A microwave generator (emitting a frequency of 500 MHz to 10 GHz) serves to irradiate the frequency having the specific band onto the biological tissues with cancer cells to allow the cancer cells spread widely on the biological tissues to be killed, after the PDT for local treatment of the biological tissues with the cancer cells has been performed to generate the ROS or heat from the photosensitizers. To improve the effectiveness of the PDT, however, the microwave vibrates the ±phonons generated from the photosensitizers having the indirect energy band gaps and generates heat. As a result, the effectiveness in the cancer therapy can be improved.

The conventional cancer therapy having a transplantation composition and a transplantation kit includes the step of irradiating optic ray onto the biological tissues with cancer cells, which is treated with photosensitizers selected from the group consisting of $TiO_2$, $ZrO_2$, $HfO_2$, and combinations thereof.

The cancer cells may originate from the biological tissues of an individual. The individual may be a vertebrate animal, especially, mammal, amphibian, reptile, bird, and the like, more especially, mammal. For example, the individual may be a human (*Homo sapiens*).

The conventional cancer therapy may further include the step of, before the treatment of the photosensitizers transplanted or attached to the biological tissues with the cancer cells, operating a microwave generator to generate a frequency of 500 MHz to 10 GHz. The frequency with a specific band, for example, the frequency of 13.56 MHz emitted from an antenna of the microwave generator moves the cancer cells to a local area within the biological tissues, so that the selectivity of the photosensitizers with respect to the cancer cells can be improved, thereby resulting in the enhancement of the effectiveness of the cancer therapy.

At the step of irradiating the optic ray onto the cancer cells, the optic ray may include pulsed infrared light, visible light, light of LED, and filtered white light source.

At the step, the photosensitizers located near the cancer cells are activated to produce the ROS that kill or necrotize surrounding cancer cells. At the step, further, cancer therapies in a cancer therapy field may be applied solely or together. For example, local therapy and systemic therapy for cancer may be applied, simultaneously, separately, or sequentially.

The PDT is less harmful to the human body than the chemotherapy using the existing anticancer agents or the radiotherapy and removes the cancer cells more effectively, and accordingly, it is expected that the PDT can be used unilaterally or used in combination with other treatment as a core technology in the cancer treatment field.

FIG. 1 shows problems the existing cancer treatments have had. According to a research of Seoul National University Hospital in Korean, the existing cancer treatments with anticancer agents have drug efflux increases, anti-apoptotic protein expression increases, target protein denaturation, low effectiveness in cold tumors, thereby resulting in anticancer drug resistance to thus cause occurrence of cancer metastasis and recurrence.

However, the optic ray (red light) used for the PDT has the limitations in permeating only by a depth of 10 mm into the body and is applicable only to the tumor existing on a superficial or local area. Further, the PDT has the limitations in performing selective transfer to the tumor tissues because of inappropriate interactions between biological molecules or aggregation among the photosensitizers. To solve these problems, studies on technologies for coupling to various carrier systems, such as micelles, sealed liposome, bio polymers, and the like have been made, but until now, they do not suggest notable results.

Prior Art—Patent Documents (Patent Document 1) Korean Patent Publication No. 10-2021-0043472 (Publication date: Apr. 21, 2021), "Photosensitization transition materials for brain cancer treatment or brain cancer removal surgery, microwave microchip for inducing movement of brain cancer cell, and use thereof", Kwangwoon University Industry-Academic Collaboration Foundation

SUMMARY

To solve the above-mentioned problems in the prior art, and an object of the present invention is to provide a photodynamic therapy and microwave therapy fusion system that is capable of allowing photosensitizers having specific indirect energy band gaps to be attached to a target tumor to locally treat solid cancer and, under the control of a microwave assisted photodynamic therapy (MWAPDT) controller, making use of i) photodynamic therapy (PDT) in which the optic ray emitted from a fiber optic probe is irradiated onto the target tumor so that reactive oxygen species (ROS) or heat is generated by the photosensitizers to locally remove the target tumor, and ii) microwave therapy in which a microwave is generated from a microwave generator, a microwave transmitter, and an antenna of a microwave probe that irradiate a specific frequency of 5.3 GHz to 10 GHz to vibrate±phonons generated by the indirect energy band gaps from the photosensitizers and generate heat, so that the target tumor is locally removed and cancer metastasis and recurrence of cancer are prevented from occurring.

To accomplish the above-mentioned objects, according to the present invention, there is provided a photodynamic therapy and microwave therapy fusion system includes one or more photosensitizers attached to the biological tissues of a site in which cancer develops, having specific indirect energy band gaps to perform photodynamic therapy for the site in which the cancer develops; and a microwave assisted photodynamic therapy (MWAPDT) controller connected to a personal computer (PC) and wherein the MWAPDT controller controls an irradiation of a microwave frequency of ranging from 5.3 GHz to 10 GHz emitted from a microwave probe, or controls an irradiation of an optic ray emitted from a fiber optic probe to be irradiated onto the biological tissues of the site in which the cancer develops, to which the photosensitizers are attached, so as to perform microwave therapy for the site in which the cancer develops, wherein the cancer is solid cancer, wherein the photosensitizers may be utilized $MeO_2$ nanoparticles selected from the group consisting of $ZrO_2$, $HfO_2$, and combinations thereof, wherein the MWAPDT controller is connected to the fiber optic probe, or the microwave probe and allows 0.01 mW to 10 W of power, a frequency of 5.3 GHz to 10 GHz of the microwave probe, to be irradiated onto the site in which the cancer develops, to which the photosensitizers are attached, thereby killing cancer cells.

The photodynamic therapy and microwave therapy fusion system of the present invention that is capable of allowing photosensitizers having specific indirect energy band gaps to be attached to a target tumor to locally treat solid cancer and, under the control of a microwave assisted photodynamic therapy (MWAPDT) controller, making use of i) photodynamic therapy (PDT) in which the optic ray emitted from a fiber optic probe is irradiated onto the target tumor so that reactive oxygen species (ROS) or heat is generated primarily by the photosensitizers as photocatalysts to locally remove the target tumor, and ii) microwave therapy in which a microwave is generated from a microwave generator, a microwave transmitter, and an antenna of a microwave probe that irradiate a specific frequency of 5.3 GHz to 10 GHz to vibrate±phonons generated by the indirect energy band gaps from the photosensitizers and generate heat, so that the target tumor is removed and cancer metastasis and recurrence are prevented from occurring.

BRIEF DESCRIPTION OF THE DRAWINGS

FIG. 2 shows materials for the research of Seoul National University Hospital in Korea, which suggest (1) photodynamic therapy (PDT) in which photosensitizers are attached to an area to be treated and light is absorbed to the area to be treated to activate the photosensitizers so that reactive oxygen species (ROS) (i.e., active oxygen) are produced from the photosensitizers to remove a target tumor locally; and (2) photothermal therapy (PTT) in which using photosensitizers, light is absorbed to an area to be treated to convert the light into heat to remove a tumor;

FIG. 4 shows reaction mechanisms of the PDT;

FIG. 5 shows photographs for microwave therapy in which microwave frequency (in the range of 5.3 GHz to 10 GHz) generated under an electromagnetic field formed by 500 MHz frequency generator is irradiated to generate heat after the optic ray emitted from a fiber optic probe is irradiated onto the target tumor through probe by using a Photodynamic therapy and Microwave therapy fusion system (PDTMTFS) controller;

FIG. 7 shows advantages of the microwave therapy providing continuous microwaves using microwave transmitters facingly attached to the biological tissues of a site in which cancer develops, on a target tumor, to thus generate heat;

DETAILED DESCRIPTION

Figure 1:
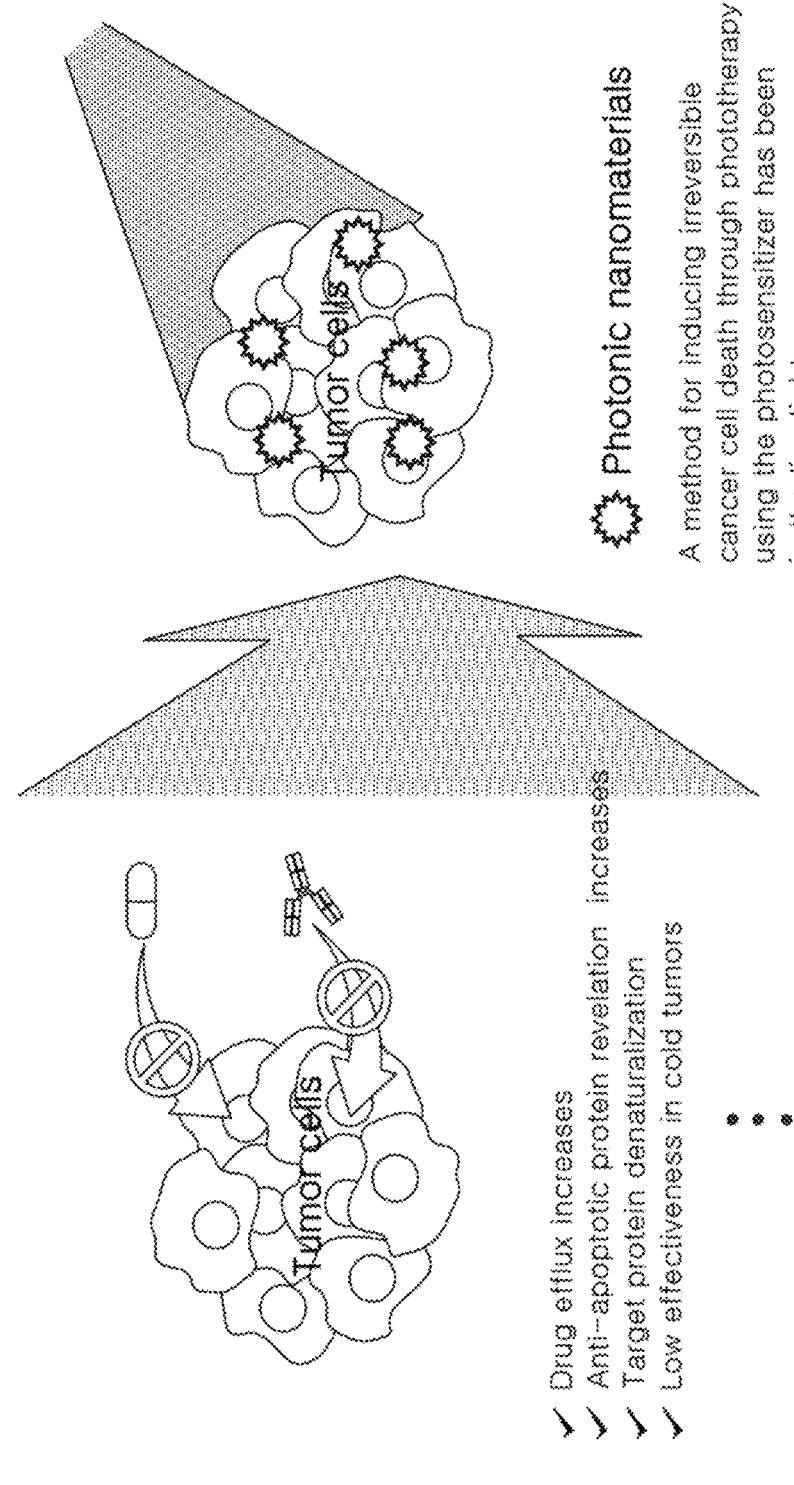
FIG. 1 shows problems the existing cancer treatments have had.

Hereinafter, embodiments of the present invention will be explained in detail with reference to the attached drawings.

In the description of the present invention, when it is determined that a detailed description of a related known technology or a known configuration may unnecessarily obscure the subject matter of the present invention, the detailed description will be omitted. In addition, when a reference numeral of a drawing indicates the same configuration, the same reference numeral is assigned in different drawings.

The term 'cancer' as used herein is defined as a disease caused by cells having aggressive characteristics so that the cells divide and grow over a normal growth limit, invasive characteristics so that the cells invade surrounding tissues, and metastatic characteristics so that the cells spread to other parts in the body. The cancer may be solid cancer, and the type of cancer according to the sites in which cancer develops is any one selected from the group consisting of brain tumor, skin cancer, stomach cancer, lung cancer, colorectal cancer, uterine cervical cancer, kidney cancer, liver cancer, prostate cancer, breast cancer, colon cancer, bladder cancer, and pancreatic cancer, and desirably, the type of cancer is brain cancer.

One of the most dangerous and hardest to treat cancer is a brain tumor.

Cancer is basically a disease of a cell cycle in which some of the body's cells divide uncontrollably to form a tumor.

The term "therapy" as used therein means all behaviors by which the symptoms of cancer come to grow better through transplantation or treatment of a composition in a tumor. For example, photodynamic therapy (PDT) is applied so that photosensitizers are administrated into the body, and laser light (optic ray) having a specific wavelength is irradiated onto a site in which cancer develops to perform a tumor treatment.

The photosensitizers are substances that are excited through an energy transfer mechanism E=hv when the optic ray of the specific wavelength is irradiated onto target tumor and generate fluorescence signals or react with surrounding substrates or oxygen to generate reactive oxygen species (ROS) or heat. The generated ROS kills or necrotizes surrounding cancer cells to provide cancer therapy effectiveness.

Recently, a method for inducing irreversible cancer cell death through phototherapy using the photosensitizers has been in the limelight.

The present invention provides a photodynamic therapy and microwave therapy fusion system (PDTMTFS) that allows photosensitizers having specific indirect energy band gaps to be attached to a target tumor to locally treat solid cancer and, under the control of a microwave assisted photodynamic therapy (MWAPDT) controller, makes use of i) photodynamic therapy (PDT) in which the optic ray emitted from a fiber optic probe is irradiated onto the target tumor so that reactive oxygen species (ROS) or heat are generated from the photosensitizers (photocatalysts) to locally remove the target tumor, and ii) microwave therapy in which a continuous wave radio frequency (CW RF) is generated from a microwave generator, a microwave transmitter, and an antenna of using a microwave probe that irradiate a frequency of 5.3 GHz to 10 GHz and ±phonons generated by the specific indirect energy band gaps from the photosensitizers are vibrated to generate heat, wherein the photodynamic therapy and microwave therapy fusion system locally removes the target tumor and prevents cancer metastasis and recurrence of cancer from occurring.

FIG. 2 shows materials for the research of Seoul National University Hospital in Korea, which suggest (1) photodynamic therapy (PDT) in which photosensitizers are attached to an area to be treated and then light is absorbed to the area to be treated to activate the photosensitizers so that reactive oxygen species (ROS) (i.e., active oxygen) are generated from the photosensitizers to locally remove a target tumor on the area to be treated; and (2) photothermal therapy (PTT) in which using the photosensitizers, light is absorbed to an area to be treated to generate heat with a temperature of 41 to 46° C. from the area to be treated so that the target tumor is removed locally with the heat.

(1) The photodynamic therapy (PDT) is a treatment in which the photosensitizers are attached to the site in which cancer develops and light is absorbed to a target tumor to activate the photosensitizers so that reactive oxygen species (ROS) are generated from the photosensitizers to locally remove the target tumor.

(2) The photothermal therapy (PTT) is a treatment in which the photosensitizers are attached to the site in which cancer develops and light is absorbed to a target tumor to generate heat with a temperature of 41 to 46° C. so that the target tumor is locally removed with the heat.

Nowadays cancer is one of the most dangerous diseases, ranking second in mortality following cardiovascular diseases. It is known that cancer is a disease of the cell cycle, when cells begin to proliferate uncontrollably, without reacting to inhibitory signals and pericellular environment, resulting in the formation of a tumor. Cancer is a multi-gene, multi-step disease originating from a single abnormal cell with an altered (mutated) DNA sequence. The emergence of tumor requires appearance of several mutagen factors in the same cell, such as an active oncogene producing a signal of uncontrolled proliferation, broken suppressor signals—the factors controlling the cell cycle, and broken mechanisms of DNA reparation which also contribute to mutagen processes. Further, cancer has six characteristics, i.e., self-sufficient growth signals, resistance to anti-growth signals, immortality of cancer cells, resistance to cell death, sustained angiogenesis for tumor feeding, invasion of cancer cells, and metastasis into other organs. To destroy cancer cells, many therapies such as surgery, chemotherapy, immunotherapy, and the like have been developed. Yet in case of inoperable tumors, for example a deep tumor in the brain, successful application of photodynamic therapy (PDT) is possible. In this method three individually non-toxic components brought together to cause harmful effects on cancer cells: photosensitizing agent, light of specific wavelength, and oxygen. Acting together, they initiate a photochemical reaction that culminates in the generation of a highly reactive product termed singlet oxygen ($^1O_2$), which can rapidly cause significant toxicity leading to cell death via apoptosis or necrosis of cancer cell. Generally, antitumor PDT effects origin from three inter-related mechanisms: direct cytotoxic effects on tumor cells, damage to the tumor vasculature, and induction of a robust inflammatory reaction that can lead to the development of systemic immunity.

At the first step, photosensitizers as special nanoparticles are administrated preliminarily into the body, which are assimilated with the help of target tumor therapy, in tumor tissues. As the photosensitizers, $MeO_2$ nanoparticles such as $ZrO_2$, $HfO_2$, and combinations thereof, which are known for their active photocatalytic and luminescence properties, can be used. Also, $MeO_2$ nanoparticles selected from the group consisting of $ZrO_2$, $HfO_2$, and combinations can be used. At the second step, by means of a special fiber optic probe, a targeted light irradiation of the tumor region is performed. Due to the absorption of optical quanta, generation of electron-hole pairs occurs in photosensitizers when electrons from the valence band pass into conduction bands.

Common photosensitizers are very unstable in excited state and emit the excess energy as fluorescence and/or heat. This state can be converted into a more stable triplet state with inverted spin of one electron. The photosensitizer in triplet state can either decay to the ground state without radiation or transfer its energy to molecular oxygen ($O_2$), which is unique in being a triplet in its ground state. In a Type I process the reactive oxygen species (ROS) are generated. The photosensitizer reacts directly with an organic molecule in a cell microenvironment, acquiring a hydrogen atom or electron to form a radical. Subsequent autoxidation of the reduced photosensitizer produces a superoxide anion radical ($O_2^{*-}$). Dismutation or one electron reduction of $O_2^{*-}$ gives hydrogen peroxide ($H_2O_2$), which in turn can undergo one-electron reduction to a powerful and virtually indiscriminate oxidant hydroxyl radical (HO*).

Figure 3:
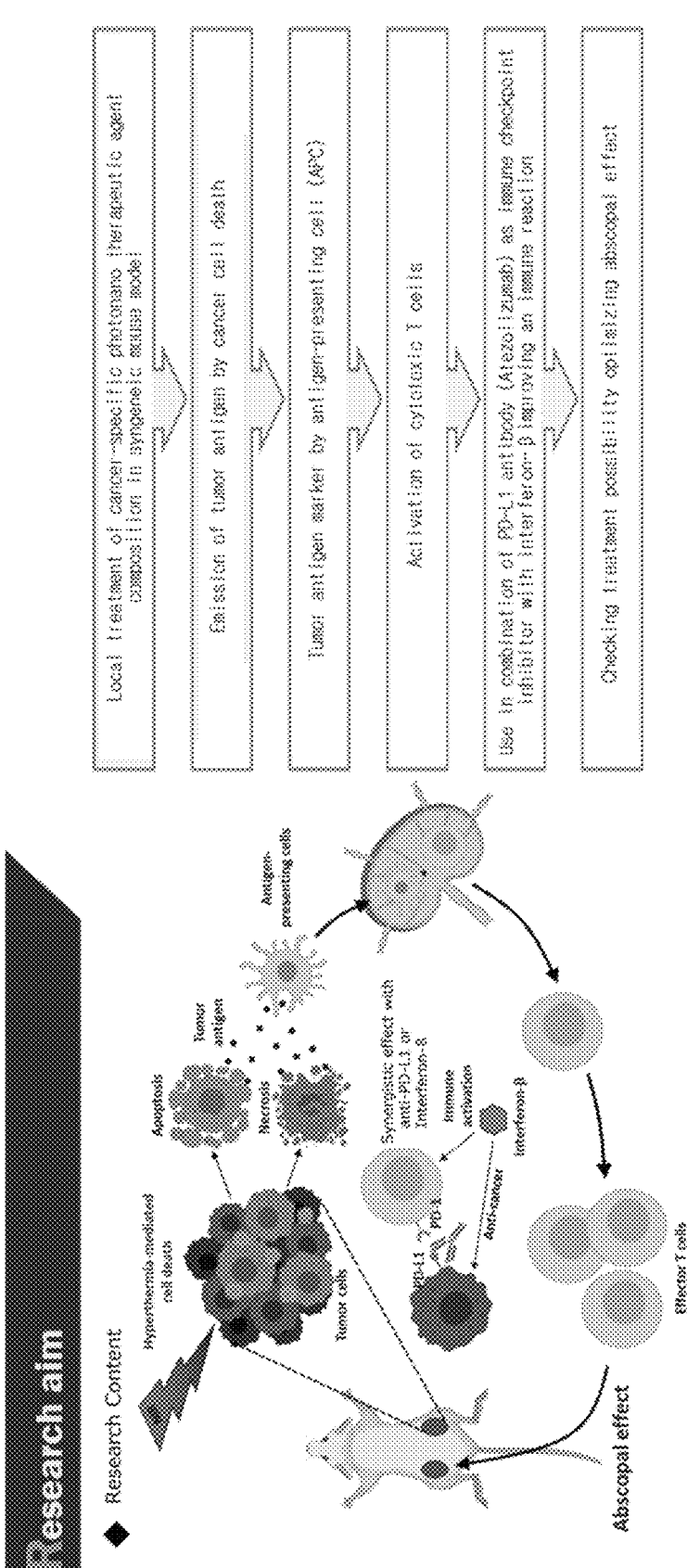
FIG. 3 shows a research aim in which cancer target (claudin-3) photosensitizers are used under the concept of FIG. 2 to perform PTT or PDT so that a target tumor is removed locally and cancer metastasis or recurrence on regions where no treatment is applied is prevented from occurring by means of activation of antitumor immunity.

FIG. 3 shows a research aim in which anti-cancer target (claudin-3) photosensitizers are used under the concept of FIG. 2 to perform PTT or PDT so that a target tumor is removed locally and cancer metastasis or recurrence on regions where no treatment is applied is prevented from occurring by means of activation of antitumor immunity.

In specific, the anti-cancer target (claudin-3) photosensitizers are used to perform PTT or PDT so that the target tumor (cancer) is locally removed and cancer metastasis or recurrence on regions where no treatment is applied is prevented from occurring by means of activation of antitumor immunity, thereby checking systemic therapy effectiveness and identifying mechanisms of abscopal effect.

Cancer therapies include surgery, radiation therapy, chemotherapy using anti-cancer agents, immunotherapy, stem cell transplantation, targeted therapy, photodynamic therapy (PDT), and microwave therapy.

In the research, microwave assisted photodynamic therapy (MWAPDT) is provided for a photodynamic therapy and microwave therapy fusion system (PDTMTFS) making use of both of the photodynamic therapy (PDT) and the microwave therapy applied to a site in which cancer develops, thereby locally treat solid cancer.

FIG. 4 shows reaction mechanisms of the photodynamic therapy (PDT).

The PDT is a treatment in which photosensitizers are used into target tumor and light of a specific wavelength is absorbed to a site in which cancer develops, so that the photosensitizers in excited states generate reactive oxygen species (ROS) and heat through an energy transfer mechanism E=hv, and chemical reactions occur by the ROS, thereby allowing the free radicals generated by single oxygen to selectively kill the cancer cells.

FIG. 5 shows photographs for microwave therapy in which microwave frequency (in the range of 5.3 GHz to 10 GHz) is irradiated to generate heat.

Figure 6:
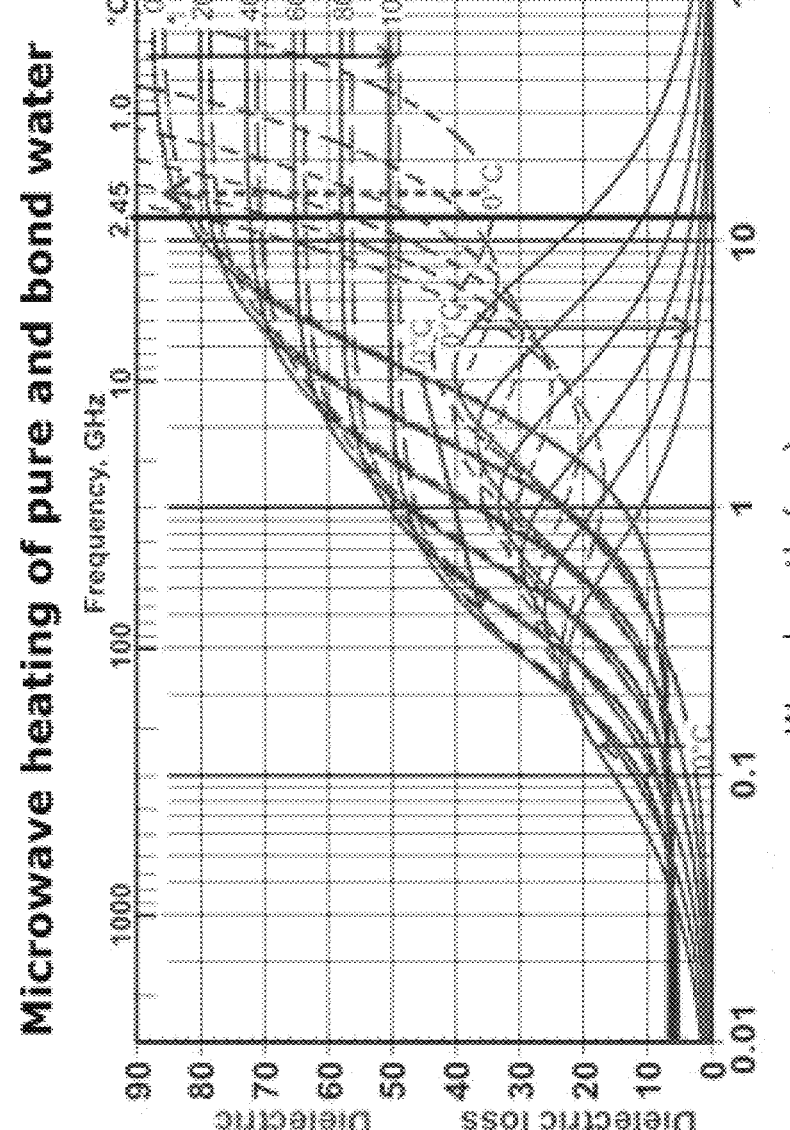
FIG. 6 is a graph showing microwave characteristics having frequency density and duration according to wavelengths and dielectric properties in microwave therapy.

FIG. 6 is a graph showing microwave characteristics having frequency density and duration according to wavelengths and dielectric properties (in microwave therapy).

FIG. 7 shows advantages of the microwave therapy providing continuous microwaves using microwave transmitters facingly attached to the biological tissues of a site in which cancer develops, on a target tumor, to thus generate heat.

Figure 8:
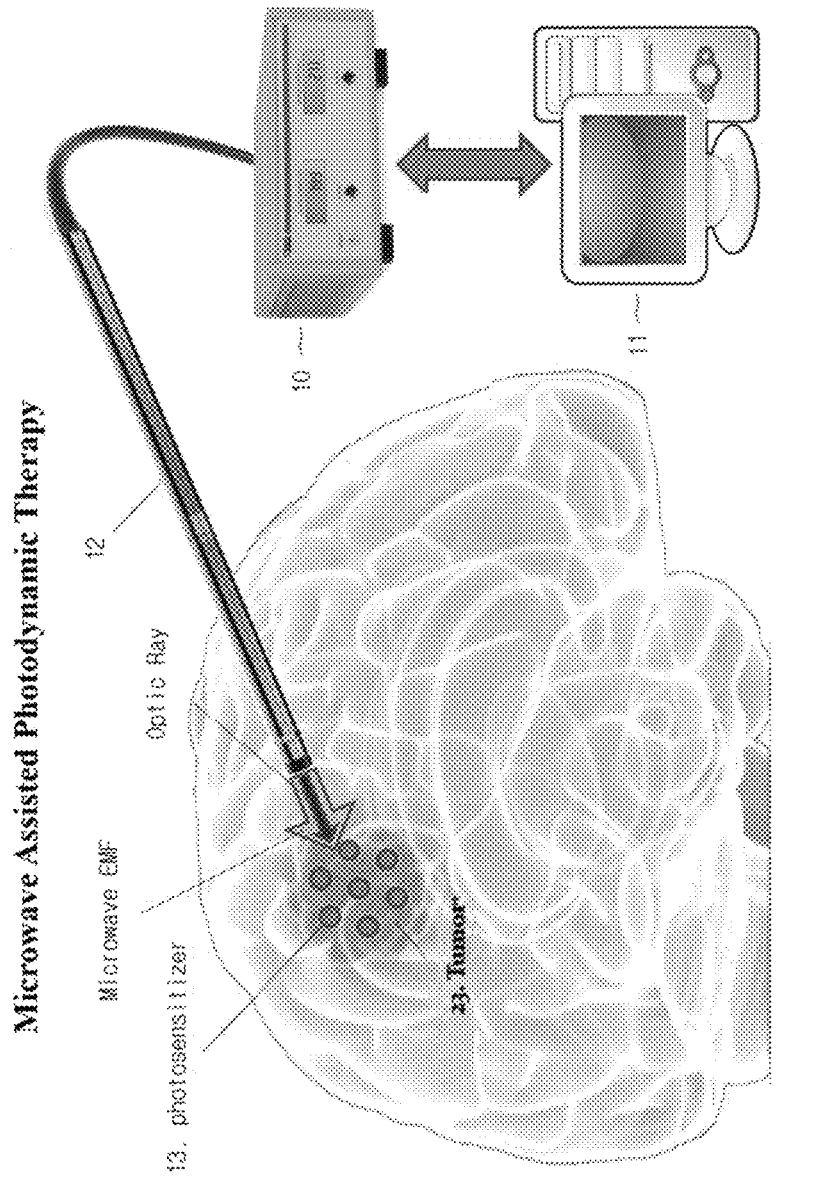
FIG. 8 is a diagram showing a photodynamic therapy and microwave therapy fusion system (PDTMTFS) according to the present invention.

FIG. 8 is a diagram showing the microwave assisted photodynamic therapy (MWAPDT) system for the PDTMTFS according to the present invention.

The photodynamic therapy and microwave therapy fusion system (PDTMTFS) according to the present invention is configured to allow one or more photosensitizers 13 to be attached to a target tumor 23 to locally treat solid cancer and, under the control of an MWAPDT controller 10, to make use of i) PDT in which the optic ray emitted from a fiber optic probe 12 is irradiated onto the target tumor 23 so that reactive oxygen species (ROS) or heat is generated from the photosensitizers to locally remove the target tumor 23, and ii) microwave therapy in which a continuous wave radio frequency (CW RF) is generated from a microwave generator, a microwave transmitter, and an antenna of a microwave probe that irradiate a microwave frequency (of 5.3 GHz to 10 GHz in an embodiment) to vibrate the ±phonons generated by indirect energy band gaps from the photosensitizers and generate heat, thereby removing the target tumor locally and preventing cancer metastasis and recurrence from occurring.

The cancer is solid cancer.

The cancer includes one of skin cancer, stomach cancer, colorectal cancer, uterine cervical cancer, kidney cancer, prostate cancer, breast cancer, brain tumor, lung cancer, liver cancer, colon cancer, bladder cancer, and pancreatic cancer.

According to the embodiment of the present invention, the photosensitizers 13 are attached to a region of brain cancer.

After the photosensitizers 13 are transplanted or attached to the target tumor 23, the microwave generator, the microwave transmitter, and the antenna of the microwave probe operate to irradiate the microwave frequency (of 5.3 GHz to 10 GHz in the embodiment) onto biological tissues with cancer cells so that the CW RF is generated to vibrate the ±phonons generated by the indirect energy band gaps from the photosensitizers and generate heat, thereby removing the target tumor 23 locally by means of the generated heat. In specific, the microwave generator, the microwave transmitter, and the antenna of the microwave probe serve to irradiate a microwave frequency of 5.3 GHz to 10 GHz using the microwave probe onto the biological tissues of the target tumor 23 so that the CW RF is generated to vibrate the ±phonons generated by the indirect energy band gaps from the photosensitizers and generate heat, thereby removing the target tumor 23 locally and preventing cancer metastasis and recurrence from occurring. The photodynamic therapy and microwave therapy fusion system (PDTMTFS) according to the present invention includes: one or more photosensitizers 13 attached to the biological tissues of the target tumor 23, the specific indirect energy band gaps; and the MWAPDT controller 10 connected to a PC 11 to perform the microwave therapy on the target tumor 23 and wherein the MWAPDT controller controls an irradiation of a microwave frequency ranging from 5.3 GHz to 10 GHz emitted from a microwave probe to be irradiated onto the biological tissues of the target tumor 23, or controls an irradiation of the optic ray emitted from the fiber optic probe 12 to be irradiated onto the target tumor 23, wherein the cancer is solid cancer, wherein the photosensitizers may be utilized $MeO_2$ nanoparticles selected from the group consisting of $ZrO_2$, $HfO_2$, and combinations thereof, wherein the MWAPDT controller is connected to the fiber optic probe, or the microwave probe and allows 0.01 mW to 10 W of power, a frequency of 5.3 GHz to 10 GHz of the microwave probe, to be irradiated onto the site in which the cancer develops, to which the photosensitizers are attached, thereby killing cancer cells.

In specific, the MWAPDT controller 10 is connected to the PC 11 to perform the microwave therapy for the target tumor 23 and adapted i) to allow the optic ray emitted from the fiber optic probe 12 to be irradiated onto the biological tissues of the target tumor 23 to which the photosensitizers 13 are attached, or ii) to allow the microwave frequency of 5.3 GHz to 10 GHz of the microwave probe 19 having the microwave generator, the microwave transmitter, and the antenna to be irradiated onto the biological tissues of the target tumor 23 to which the photosensitizers 13 are attached to generate the CW RF from the microwave transmitter so that the ±phonons are vibrated by the specific indirect energy band gaps to generate heat, thereby removing the target tumor locally by means of the generated heat.

As the photosensitizers 13, $MeO_2$ nanoparticles selected from the group consisting of $ZrO_2$, $HfO_2$, and combinations thereof are used.

The MWAPDT controller 10 is connected to the fiber optic probe, or the microwave probe respectively and allows 0.01 to 100 mW of power, a frequency of 5.3 GHz to 10 GHz of the microwave probe, to be irradiated onto the target tumor 23 to which the photosensitizers 13 are attached, thereby killing the cancer cells.

According to the embodiment of the present invention, the PDTMTFS according to the present invention is configured to allow the photosensitizers 13 to be attached to the target tumor 23 to locally treat solid cancer and, under the control of the MWAPDT controller 10, makes use of i) the PDT in which the optic ray emitted from the fiber optic probe 12 is irradiated onto the target tumor 23 to which the photosensitizers 13 are attached so that the ROS as photocatalysts or heat is generated to locally remove the target tumor 23, and ii) the microwave therapy in which a continuous wave radio frequency (CW RF) is generated from the microwave transmitter of the microwave probe irradiating a microwave frequency of 5.3 GHz to 10 GHz to generate heat by means of the vibration of the ±phonons generated by the indirect energy band gaps, thereby removing the target tumor locally and preventing cancer metastasis and recurrence from occurring.

Figure 9:
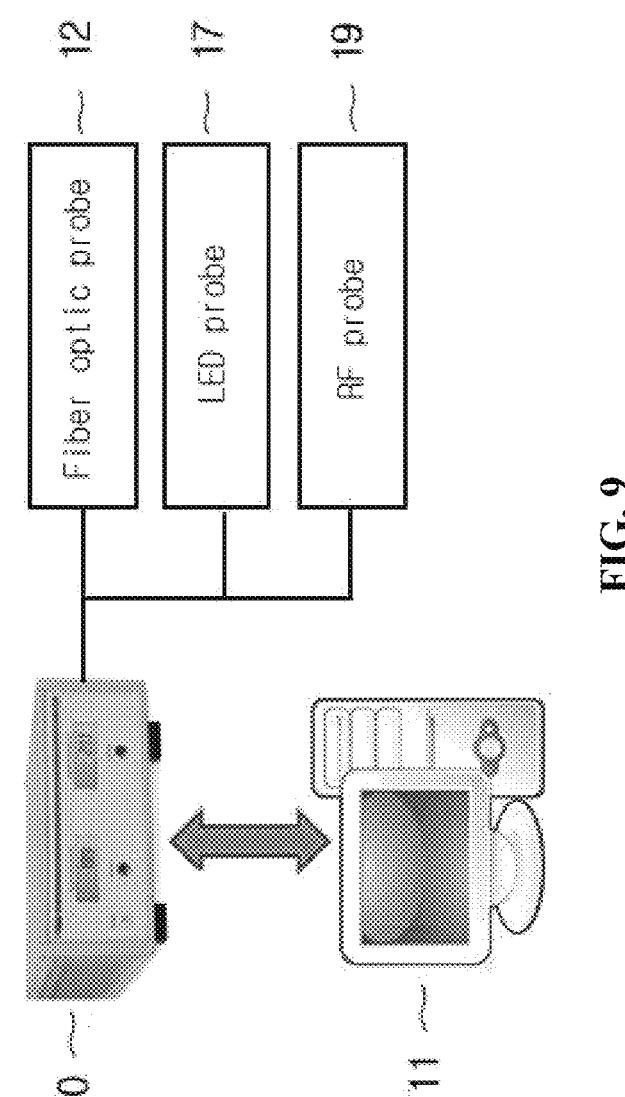
FIG. 9 is a diagram showing a fiber optic probe, an LED probe, and a microwave probe operating cooperatively with a PDTMTFS controller according to the present invention.

FIG. 9 is a diagram showing the fiber optic probe 12, the LED probe 17, and the microwave probe 19 operating cooperatively with the MWAPDT controller 10.

The MWAPDT controller 10 is connected to the fiber optic probe 12, and the fiber optic probe 12 includes an operating button, a controller, a fiber optic driving circuit, and an optical fiber connected to a fiber optic driver and shielded in a longitudinal direction, so that the optic ray emitted from an optical fiber is irradiated onto the biological tissues of the target tumor 23 to which the photosensitizers 13 are attached to thus generate the ROS or heat from the photosensitizers 13, thereby removing the target tumor 23 locally by means of the generated ROS or heat.

The MWAPDT controller 10 is connected to the microwave probe 19, operates cooperatively with the fiber optic probe 12, and the microwave probe 19 includes an operating button, a controller, a battery, a microwave generator having an oscillator, a modulator, a bandpass filter, and an amplifier, a microwave transmitter, and an antenna, so that the microwave frequency of 5.3 GHz to 10 GHz is irradiated onto the biological tissues of the target tumor 23 to which the photosensitizers 13 are attached, together with the optic ray irradiated onto the biological tissues of the target tumor 23, and accordingly, the target tumor 23 becomes hot by ±phonons in the excitation band to generate heat with a temperature of 41 to 46° C., thereby killing the cancer cells.

Further, the microwave probe 19 further includes a short range wireless communication part (Bluetooth™) connected to the controller turned on or off by the operating button, and the microwave probe 19 operates cooperatively with a smartphone, a tablet PC, or the PC 11 and is controlled by remote operational commands (on or off).

Figure 10:
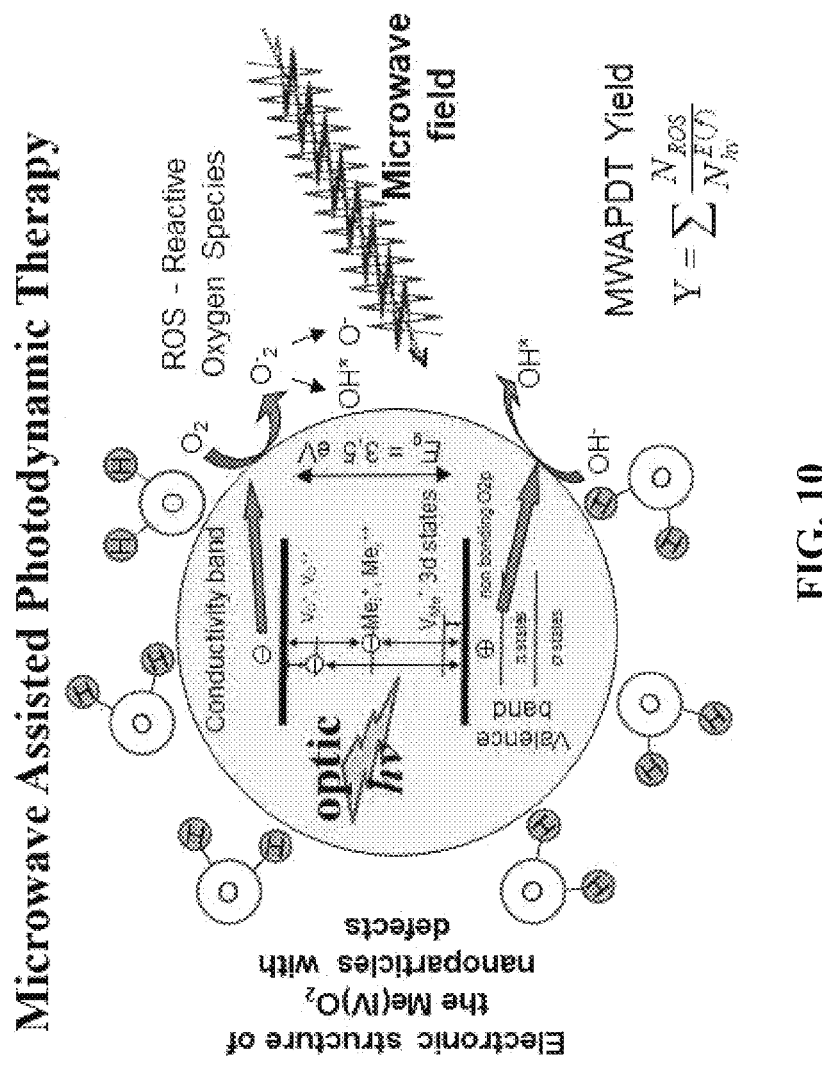
FIG. 10 shows an electronic structure of $TiO_2$ nanoparticles with defects in the band gaps and ROS producing path.

FIG. 10 shows an electronic structure of $TiO_2$ nanoparticles with defects in the band gaps and ROS producing paths.

In case of $TiO_2$ nanoparticles, ROS generation can be provided by excitation and output of electron-hole pairs on the surfaces of $TiO_2$ nanoparticles. It is known that $TiO_2$ is a broadband semiconductor with the gap (Eg) of 3.0 and 3.2 eV with respect to rutile and anatase, respectively. In the case of $TiO_2$ nanoparticles, Eg can increase to 3.5 eV. In connection with this, the excitation of $TiO_2$ nanoparticles is manifested only after irradiation by a UV source of a wavelength of less than 380 nm. The generation efficiency of the ROS is determined by two factors: (a) the quantum yield, i.e., the ratio of absorbed photons generating electron-hole pairs with respect to the number of charge carriers taking part in useful reactions, and (b) the spectrum of catalyst action.

It is known that both the regions of charge carrier capturing (traps), which prevent their exit to the surfaces of the nanoparticles, and a reduction in Eg, which increases the probability of electron-hole pairs recombining, can negatively affect the catalyst efficiency. Structural defects may serve as traps for charge carriers (oxygen vacancies, titanium interstitials, etc.). A decrease in Eg can occur by the formation of impurity levels near the valence band (VB) and the conduction band (CB). Further, the appearance of additional levels in the band gap and a decrease of Eg influence the spectrum of action of the catalyst by increasing the percentage of the absorbed useful energy when being irradiated by a light. The ablated $TiO_2$ nanoparticles have a large specific surface area due to a small average size of approximately 10 nm. Further, the Eg increases as the sizes of the nanoparticles reduce, thereby causing a decrease in the probability of recombination of the electron-hole pairs. Also, the ablated nanoparticles possess a high concentration of surface defects which can affect the generation of ROS on the surfaces of the nanoparticles ablated in two ways. Further, the defects are the traps for charge carriers preventing their migration to the surfaces of the $TiO_2$ nanoparticles. However, the defects form donor and acceptor levels located near the conductivity band and the valence band, respectively, thereby increasing the concentration of the charge carriers. In addition, the defects on the surfaces of the nanoparticles can be active centers for the formation of the absorbed radicals. Accordingly, the production of the $TiO_2$ nanoparticles possessing high PDT activity can be a very topical experimental subject.

As the photosensitizers 13, $MeO_2$ nanoparticles such as $ZrO_2$, $HfO_2$, and combinations thereof can be used. Also, $MeO_2$ nanoparticles selected from the group consisting of $ZrO_2$, $HfO_2$, and combinations thereof can be used.

The photosensitizers 13 attached to the target tumor 23 can be used (a) $TiO_2$ nanoparticles, (b) 0.1 to 0.5 $Mn$—$TiO_2$ with 10 to 50 wt % Mn content, or (c) 0.3 $Co$—$TiO_2$.

For example, the photosensitizers 13 may be used 0.1 to 0.5 $Mn$—$TiO_2$ with 10 to 50 wt % Mn content.

Figure 11:
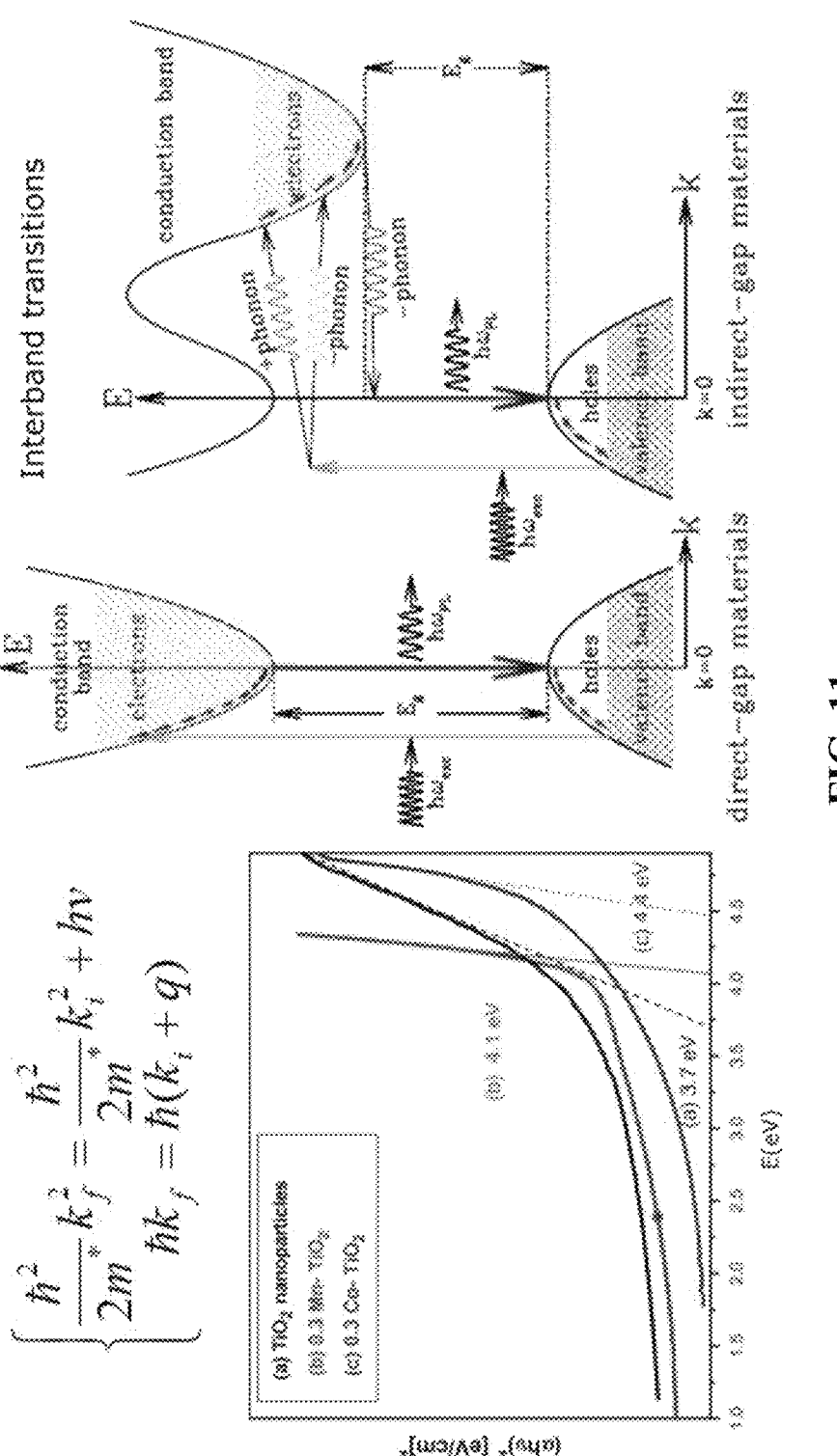
FIG. 11 shows, in case of using an LED, upon the application of the MWAPDT for irradiating electromagnetic waves of specific wavelength and frequency using (a) $TiO_2$ nanoparticles, (b) 0.3 Mn—$TiO_2$, and (c) 0.3 Co—$TiO_2$, when supplied an electric field (E=hv) of (a) 3.7 eV, (b) 4.1 eV, and (c) 4.4 eV respectively, displays the E-k plot between the electric field (E) and kinetic energy k having direct and indirect semiconductor characteristics, in accordance with lattice matching and energy-momentum conservation laws, the excitation from the valance band to the conduction band occurs in a compound semiconductor of a Gallium Arsenide (GaAs) LED. Indirect photo catalysis is generated±phonons by indirect energy band gaps, and is used microwave treatment and PDT fusion technologies to remove cancer by generating heat while±phonons vibrate repeatedly by means of the lattice vibrations caused by microwave.

FIG. 11 shows, in case of using the LED, upon the application of the PDTMTFS for irradiating electromagnetic waves of specific wavelength and frequency using (a) $TiO_2$ nanoparticles, (b) 0.3 $Mn$—$TiO_2$, and (c) 0.3 $Co$—$TiO_2$, when supplied an electric field (E=hv) of (a) 3.7 eV, (b) 4.1 eV, and (c) 4.4 eV respectively, displays the E-k plot between the electric field (E) and kinetic energy k having direct and indirect semiconductor characteristics, in accordance with lattice matching and energy-momentum conservation laws, the excitation from the valance band to the conduction band occurs in a compound semiconductor of a Gallium Arsenide (GaAs) LED, electron-hole pairs are recombined, photons are generated according to a band gap, attractive forces among atoms in a solid are generated by the Coulomb force law, and as distances among the particles decrease and increase repeatedly by means of the lattice vibrations caused by pulse waves, phonons are generated.

In the case of using the LED light emitted from the LED of the LED probe 17, a direct semiconductor has band-to-band recombination very frequently occurring when k=0, and accordingly, the GaAS semiconductor having high recombination rate of electron-hole pairs can be used. On the other hand, in the E-k plot of the indirect semiconductor, the bottom of the conduction band does not lie when k=0, and in this case, like the direct semiconductor, the electron-hole pairs cannot be recombined. If it is desired to emit photons, the momentum k has to be varied, and further, the absorption or emission of the phonons representing lattice vibrations as particles has to be provided. The absorption or emission of the phonons causes carriers to move a horizontal axis of the E-k plot to thus induce the recombination of electron-hole pairs, and as the photons are emitted, the carriers move a horizontal axis. Representative examples of the indirection semiconductor include silicon (Si) and germanium (Ge).

According to the embodiment of the present invention, the MWAPDT controller 10 is connected to the fiber optic probe 12 and controls the fiber optic probe 12 so that the optical fiber driving circuit operates by the operating button to irradiate the optic ray emitted from the optical fiber of the fiber optic probe 12 onto the biological tissues of the target tumor 23 to which the photosensitizers 13 are attached.

The MWAPDT controller 10 is connected to the microwave probe 19, operates cooperatively with the fiber optic probe 12 respectively.

The microwave probe 19 includes an operating button, a controller, a battery, a microwave generator having an oscillator, a modulator, a bandpass filter, and an amplifier, a microwave transmitter, and an antenna.

The microwave frequency of 5.3 GHz to 10 GHz emitted from the microwave probe 19 is irradiated onto the biological tissues of the target tumor 23 to which the photosensitizers 13 are attached, and accordingly, the CW RF is generated from the microwave generator, the microwave transmitter, and the antenna of the microwave probe 19 to vibrate the #phonons generated by the indirect energy band gaps from the photosensitizers 13 and generate heat from the biological tissues of the target tumor 23 to which the photosensitizers 13 are attached, thereby removing the target tumor 23 locally and preventing cancer metastasis and recurrence from occurring.

According to the present invention, microwave assisted photodynamic therapy system (MWAPDT), that is, the photodynamic therapy and microwave therapy fusion system: PDRMTFS) is configured to allow the photosensitizers to be attached to the target tumor to locally treat solid cancer and, under the control of the MWAPDT controller, makes use of i) the PDT in which the optic ray emitted from the fiber optic probe is irradiated onto the target tumor, so that the ROS or heat are (is) generated from the photosensitizers to locally remove the target tumor, and ii) the microwave therapy in which the CW RF is generated from the microwave transmitter irradiating the specific microwave frequency of 5.3 GHz to 10 GHz emitted from the microwave probe so that the ±phonons generated by the indirect energy band gaps from the photosensitizers are vibrated to generate heat, thereby removing the target tumor locally and preventing cancer metastasis and recurrence from occurring.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A photodynamic therapy and microwave therapy fusion system comprising:

one or more photosensitizers configured to be attached to the biological tissues of a site in which cancer develops, having specific indirect energy band gaps to perform photodynamic therapy for the site in which the cancer develops; and a microwave assisted photodynamic therapy (MWAPDT) controller connected to a personal computer (PC), wherein the MWAPDT controller controls an irradiation of a microwave frequency ranging from 5.3 GHz to 10 GHz emitted from a microwave probe, or controls an irradiation of an optic ray emitted from a fiber optic probe to be irradiated onto the biological tissues of the site in which the cancer develops, to which the one or more photosensitizers are configured to be attached, so as to perform microwave therapy for the site in which the cancer develops, wherein the cancer is solid cancer, wherein the one or more photosensitizers uses $MeO_2$ nanoparticles selected from the group consisting of $ZrO_2$, $HfO_2$, and combinations thereof, and wherein the MWAPDT controller is connected to the fiber optic probe, or the microwave probe and allows 0.01 mW to 10 W of power, a frequency of 5.3 GHz to 10 GHz of the microwave probe, to be irradiated onto the site in which the cancer develops, to which the one or more photosensitizers are attached, thereby killing cancer cells.

2. The system according to claim 1, wherein the cancer includes one of skin cancer, stomach cancer, colorectal cancer, cervical cancer, kidney cancer, prostate cancer, breast cancer, brain tumor, lung cancer, liver cancer, uterine cervical cancer, colon cancer, bladder cancer, and pancreatic cancer.

3. The system according to claim 1, wherein the MWAPDT controller is connected to the fiber optic probe, and the fiber optic probe comprises an operating button, a controller, a fiber optic driving circuit, and an optical fiber connected to a fiber optic driver and shielded in a longitudinal direction, so that the optic ray emitted from an optical fiber is irradiated onto the biological tissues of the site in which the cancer develops, to which the one or more photosensitizers are attached, to thus generate reactive oxygen species (ROS) or heat by the one or more photosensitizers thereby removing a target tumor locally.

4. The system according to claim 3, wherein the MWAPDT controller is additionally connected to the microwave probe, and the microwave probe comprises an operating button, a controller, a battery, an RF generator having an oscillator, a modulator, a bandpass filter, and an amplifier, an RF transmitter, and an antenna, so that the optic ray and the microwave frequency of 5.3 GHz to 10 GHz are irradiated onto the biological tissues of the site in which the cancer develops, to which the one or more photosensitizers are attached, and the biological tissues become hot by ±phonons in an excitation band by the indirect energy band gaps and generate heat with a temperature of 41 to 46° C. to kill cancer cells, on the target tumor.

* * * * *